US007192556B2

(12) United States Patent
Hamacher et al.

(10) Patent No.: US 7,192,556 B2
(45) Date of Patent: Mar. 20, 2007

(54) FLOW CELL, METHOD FOR SEPARATING CARRIER-FREE RADIONUCLIDES, AND THE RADIOCHEMICAL REACTION THEREOF

(75) Inventors: Kurt Hamacher, Aachen (DE); Willi Bolten, Jülich (DE)

(73) Assignee: Forschungszentrum Julich GmbH, Julich (DE)

( * ) Notice: Subject to any disclaimer, the term of this patent is extended or adjusted under 35 U.S.C. 154(b) by 51 days.

(21) Appl. No.: 10/506,022

(22) PCT Filed: Feb. 6, 2003

(86) PCT No.: PCT/DE03/00332

§ 371 (c)(1),
(2), (4) Date: Aug. 26, 2004

(87) PCT Pub. No.: WO03/073437

PCT Pub. Date: Sep. 4, 2003

(65) Prior Publication Data

US 2005/0167267 A1 Aug. 4, 2005

(30) Foreign Application Priority Data

Feb. 28, 2002 (DE) .............................. 102 08 668

(51) Int. Cl.
*G01N 21/00* (2006.01)
*C25B 7/00* (2006.01)
*C25B 11/00* (2006.01)
*C25B 1/00* (2006.01)
*C25F 5/00* (2006.01)
*C25F 1/00* (2006.01)
*C02F 1/461* (2006.01)
*F03H 1/00* (2006.01)

(52) U.S. Cl. ......................... 422/57; 204/450; 204/600; 205/43; 205/688; 205/702; 205/755; 205/760; 313/359.1

(58) Field of Classification Search ................ 204/450, 204/600; 205/43, 688, 702, 755, 760; 422/57
See application file for complete search history.

(56) References Cited

U.S. PATENT DOCUMENTS 4,780,642 A * 10/1988 Jacquot .................... 313/359.1
5,770,030 A    6/1998 Hamacher et al.

FOREIGN PATENT DOCUMENTS

DE    101 08 440      10/2002
JP    2001 281131     10/2001

\* cited by examiner

*Primary Examiner*—Jill Warden
*Assistant Examiner*—Lore Ramillano
(74) *Attorney, Agent, or Firm*—Andrew Wilford

(57) ABSTRACT

The invention relates to a flow cell, a method for separating carrier-free radionuclides from a liquid or liquefiable target material, and the radiochemical reaction thereof. According to prior art, flow cells are known which require reaction volumes corresponding to the volume of the target material in order to carry out the desired reactions. The inventive flow cell (1) and method enable the reaction volume, and thus the quantity of starting material, to be reduced by a multiple by reducing the cylinder volume (=reaction volume). As the radioactively marked product is present in very small quantities (picomole to nanomole), the HPL-chromatographic separation of the non-reacted starting material is significantly improved. The economic efficiency of the method is increased due to the fact that small quantities of starting material can be used.

12 Claims, 3 Drawing Sheets

FLOW CELL, METHOD FOR SEPARATING CARRIER-FREE RADIONUCLIDES, AND THE RADIOCHEMICAL REACTION THEREOF

CROSS REFERENCE TO RELATED APPLICATIONS

This application is the US national phase of PCT application PCT/DE03/00332, filed 6 Feb. 2003, published 4 Sep. 2003 as WO 03/073437, and claiming the priority of German patent application 10208668.0 itself filed 28 Feb. 2002.

FIELD OF THE INVENTION

The invention relates to a flow cell as well as to a method of separating carrier-free radionuclides from liquids or liquefiable target material and their radiochemical reactions.

BACKGROUND OF THE INVENTION

Radionuclides can be made by nuclear conversion processes in a cyclotron, for example by reirradiating a suitable target with protons. An exact description of a method of separating carrier-free radionuclides from a target liquid is known, for example, from German patent DE 195 00 428.

From German patent document DE 195 00 428 a device is also known (a flow cell) for the separation of carrier-free radionuclides from a target liquid, which is comprised substantially of a cylinder of a carbon glass (Sigradur®) and an axial platinum cannula through which a cylindrical vessel can be filled or emptied through which the inert gas can be fed into the chamber. The system is fixed by means of a plastic support and is sealed. At the lower end a flat funnel is worked which opens into the duct carrying off the water. In the head of the support, there is a gas feed line as well as an opening through which the gas can be discharge. The cylinder of carbon glass (Sigradur®) and the platinum cannula are connected to a direct current source and can be switched to serve either as the cathode or anode. For the recovery of the desired radionuclide, for example, ($^{18}$F) fluoride from ($^{18}$O)H$_2$O, the flow cell is filled with ($^{18}$F) fluoride containing target water. The ($^{18}$F) fluoride is indirectly deposited on the surface of the cylinder and the ($^{18}$O) water is transported out of the latter. The height of the zone at which the ($^{18}$F) fluoride is indirectly fixed is identical with the level of the ($^{18}$O) water in the cell.

In order that the radio isotope fixed on the surface can be completely transferred to another liquid phase by reversal of the polarity of the electric filled, it is necessary to match the level in the cell to which the latter was filled with the ($^{18}$O) water. For the subsequent ($^{18}$F) fluoridation, therefore, a reaction volume must be provided which corresponds to that of the target water. Thus it is necessary to match the quantity of the educt so that it corresponds at the optimal educt concentration to this volume (for example 1.3 ml). Because of the very small quantities or proportions of these products (picomoles to nanomoles) with respect to the proportion of unoriented educt (μmol), difficulties in separation occur during purification and especially during chromatographic purefaction. Since the mass of the educt significantly exceed the mass of the product, an HPL-chromatographic separation can only run with poor resolution.

OBJECT OF THE INVENTION

It is thus an object of the invention to provide a device and a method whereby the reaction volume can be reduced. It is a further object of the invention to reduce the amount of material of the educt by a multiple while maintaining the optimum educt concentration.

SUMMARY OF THE INVENTION

The objects are attained according to the invention in that there is a gap between the cylinder and the piston.

With the flow cell according to the invention and the method, it is possible directly to reduce the cylinder volume (=reaction volume) and thereby reduce the quantity of the educt also by a multiple. The reduction of the quantity of the educt simplifies the chromatographic purification and enables a quantitative separation of the carrier-poor marker compound (product) from the educt. Since the reduced educt quantities can be used, the costs are reduced and the economy of the method enhanced.

BRIEF DESCRIPTION OF THE DRAWING

The drawing shows an embodiment of the method and the device according to the invention by way of example. In the drawing.

SPECIFIC DESCRIPTION

Figure 1:
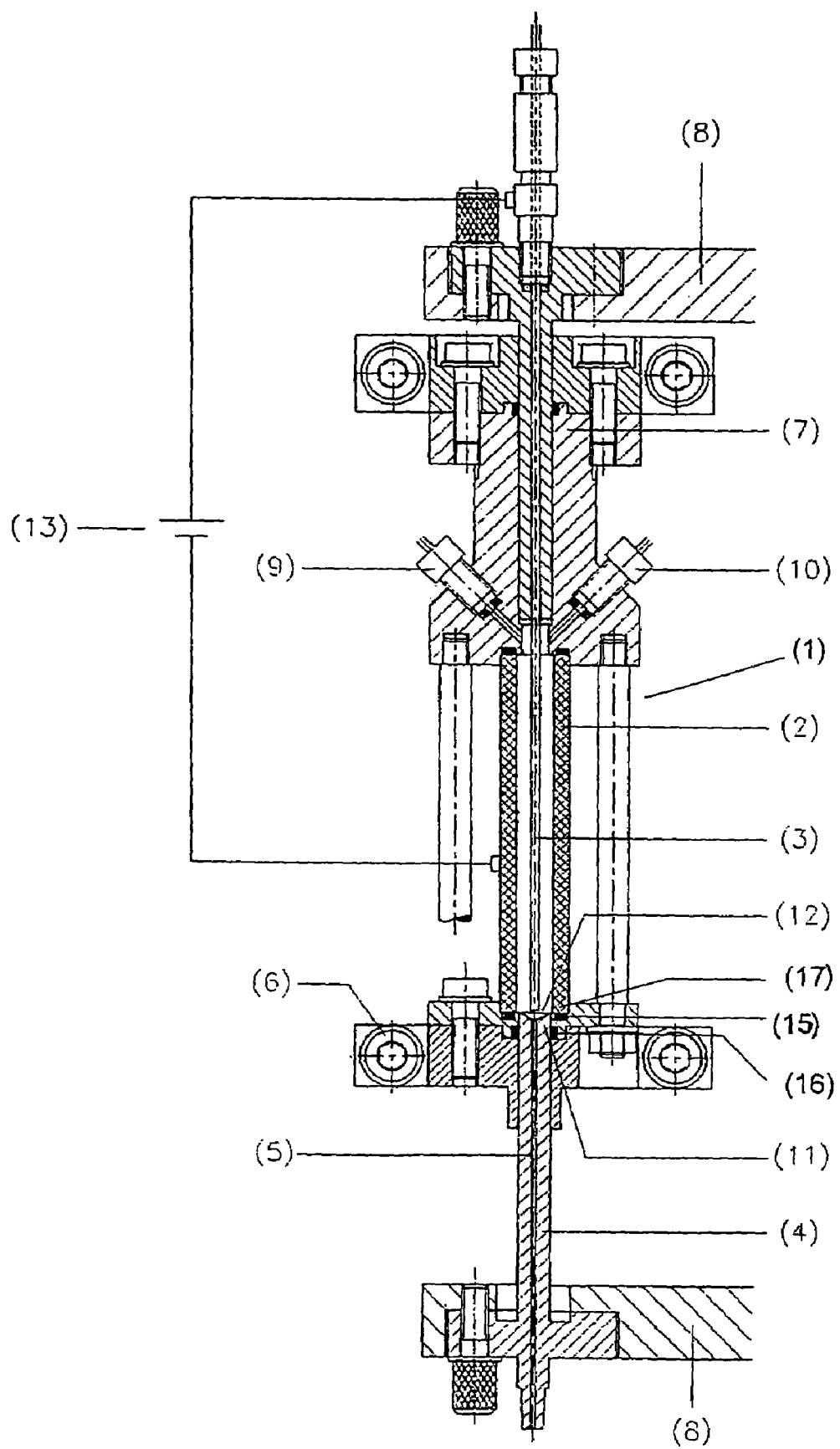
FIG. 1 is a cross section through the flow cell in an end position I.

FIG. 1 shows the flow cell 1 with a cylinder 2 receiving a cannula 3 which is bounded from below by a piston 4 with a bore 5 connected by a yoke 6 with a cannula holder 7. The cylinder 2 can be filled with liquid or inert gas through the cannula 3. The flow cell 1 is fixed by a support 8 and sealed. In the head part of the support 8, there are two feed lines 9 and 10 through which the gases can be fed to the device or carried away. In the head of the piston 11, there is a flat funnel 12 which opens into a bore 5. The cylinder 2 and the cannula 3 are connected to a direct current source 13 and can be selectively switched for use as the cathode or anode. In position I, the cannula 3 is located at the lower end of the cylinder 2. The piston 4 is located outside the cylinder 2. In the lower region 17 of the cylinder 2, two sealing rings 15 and 16 seal the piston 4 with respect to the cylinder 2.

Figure 2:
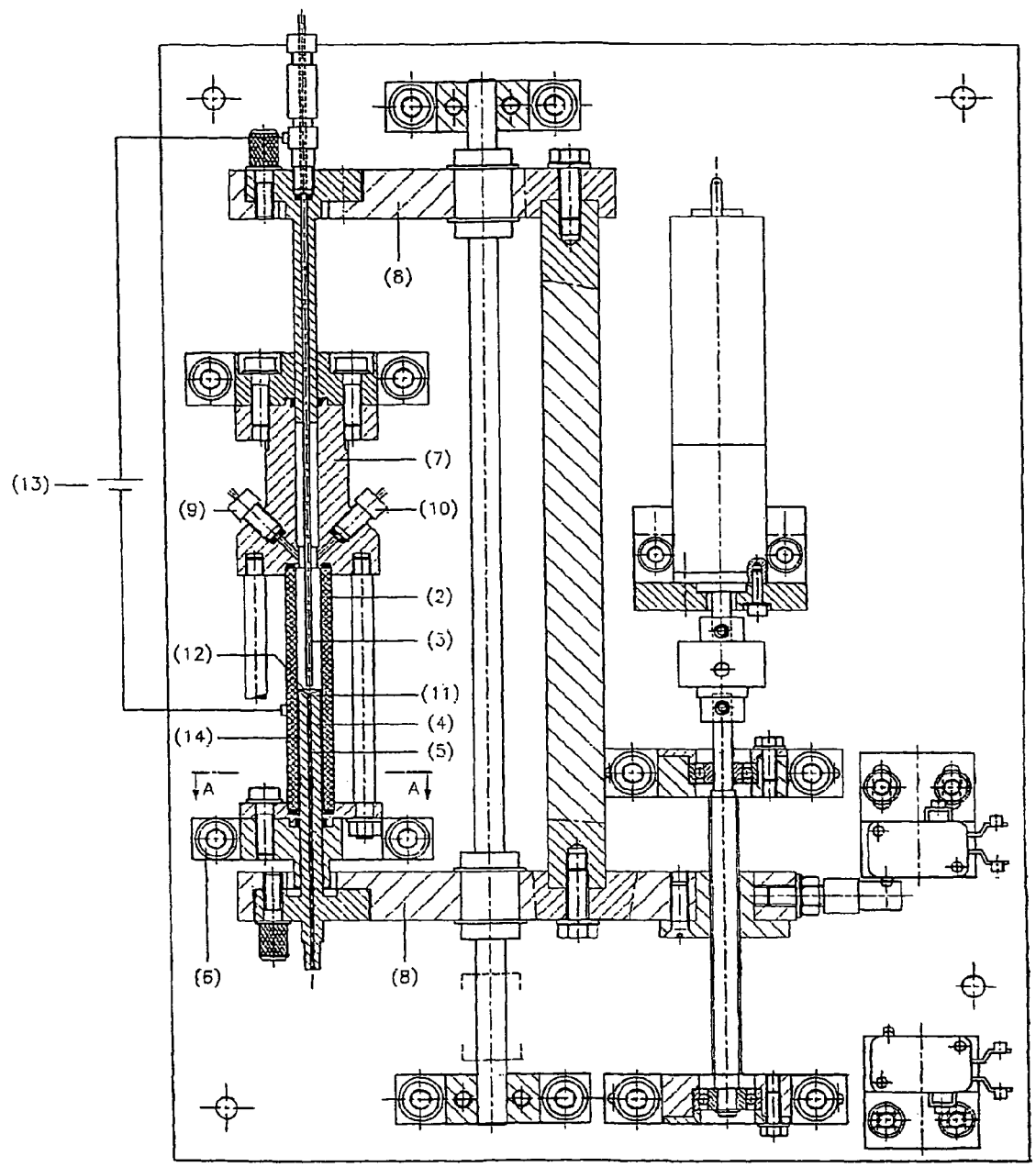
FIG. 2 is a cross section through the flow cell in an opposite end position II.

In FIG. 2 the same features of the device have been represented by the same reference numerals. FIG. 2 shows the arrangement of the components of the flow cell 1 in Position II, with the piston 4 shifted into the cylinder 2. The cannula 3 is pushed out of the cylinder 2 by the amount to which the piston 4 projects into the cylinder 2. Between the piston 4 and the cylinder 2, an annular gap 14 is formed. In FIG. 2 at the lower portion of the cylinder, a section plane has been marked by the reference character "A".

Figure 3:
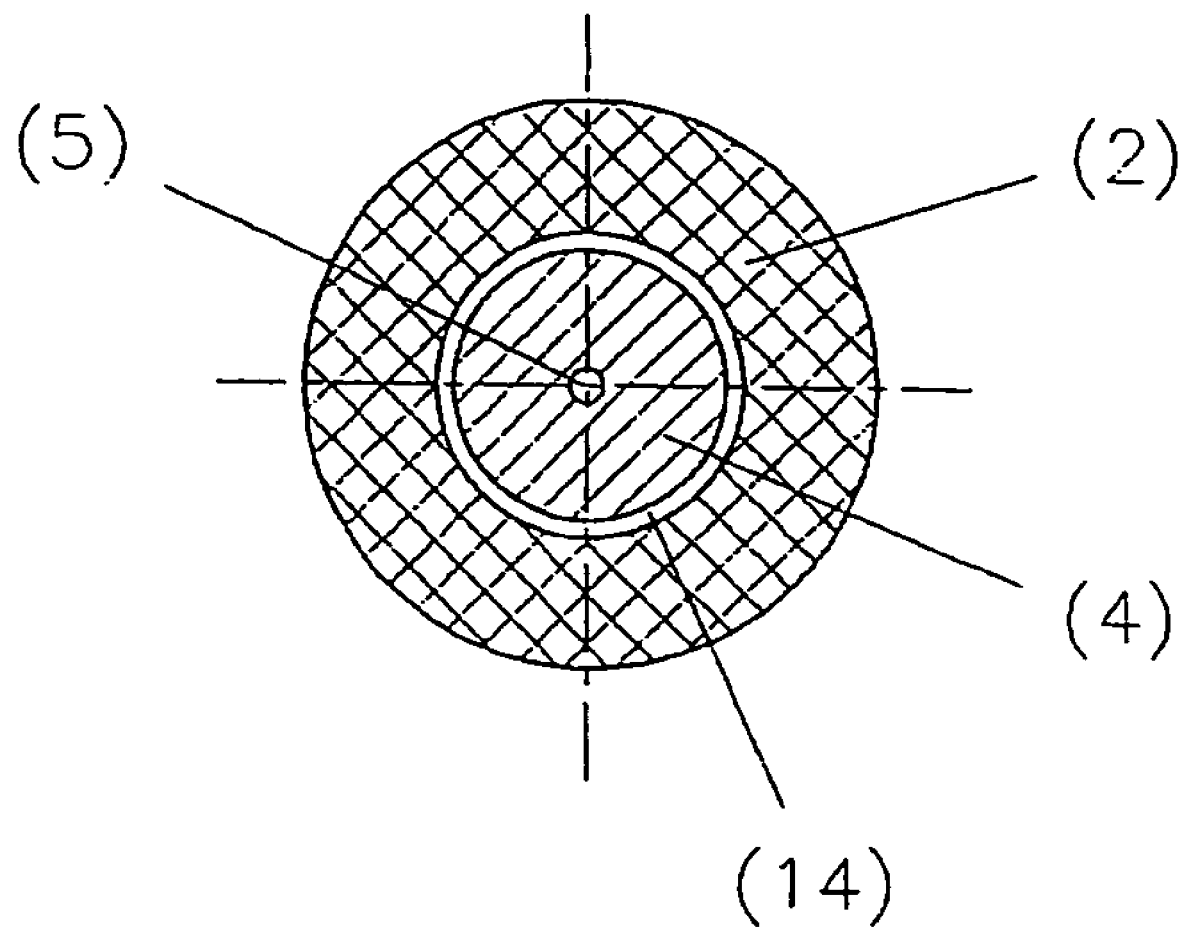
FIG. 3 is cross section taken along line A—A of FIG. 2.

FIG. 3 shows the flow cell 1 in position II in a section along the section plane A. The annular gap 14 can be seen between the piston 4 and the cylinder 2.

The invention is described by way of example below.

At the beginning of the reaction the components of the flow cell 1 are arranged, for example, as follows (see also FIG. 1; Position I); the lower opening of the cannula 3, which is preferably made from platinum is located at the lower end 17 of the cylinder 2 and the piston 4 is located externally of the cylinder 2. The flow cell 1 is filled through the bore 5 or the duct 3 with the ($^{18}$F) fluoride containing target water, whereby the ($^{18}$F) fluoride is anodically deposited on the surface of the cylinder 2 to which a DC voltage of, for example, 20 volts is applied via the DC voltage source 13. The cannula 3 here serves as the cathode. The cylinder 2 is made in an advantageous embodiment of the device of a pore-free inert material, like for example carbon glass (Sigradur®), a noble metal or platinum.

The piston 4 should preferably be made from an inert material. As suitable material, for example PEEK (polyetheretherketon), quartz glass or implement glass have been found to be suitable. It is, however, also possible to use a piston of an electrically conductive material which can then also be used as an electrode. The gap width or the difference in radius between the cylinder 2 and the piston 4 is dependent upon the fabrication method. Preferred is a radius difference between the cylinder 2 and the piston 4 of 0.4 mm. Suitable however also are gap widths of <0.2 mm. For the ratio of the radii between the cylinder ($r_1$) and the piston ($r_2$), the following equations can apply:

$$F_1 = r_1^2 * \Pi \text{ where } F_1 = \text{the area of the cylinder 2}$$

$$F_2 = r_2^2 * \Pi \text{ where } F_2 = \text{the area of the piston 4}$$

$$F_3 = F_1 - F_2 = \Pi(r_1^2 - r_2^2) \text{ where } F_3 = \text{the area of the gap 14}$$

$$V_3 = r_1^2 - r_2^2 = (r_1 + r_2)(r_1 - r_2)$$

where $V_3$ = the volume of the gap 14

$$V_1/V_3 = r_1^2/r_1^2 - r_2^2 = r_1^2/(r_1 + r_2)(r_1 - r_2)$$

where $V_1$ = the volume of the cylinders 2

After the filling of the flow cell with the target solution (for example $^{18}$O water), the radio isotope (for example $^{18}$F fluoride) is deposited on the inner surface of the cylinder 2 and the $^{18}$O water is transported out of the flow cell 1 through the bore 5 in the piston 4. The height of the zone in which the ($^{18}$F) fluoride is anodically fixed, corresponds to the fill level of the $^{18}$O water in the cylinder 2. The ($^{18}$F) fluoride fixed on the surface of the cylinder 2 is then completely dissolved in another liquid phase like for example an organic phase transfer catalyst containing solution (($K \subset 2.2.2$)$_2$C$_2$O$_4$ in dimethylsulfoxide=DMSO) by reversal of the electrical field. For that purpose it is necessary that the fill level of this liquid phase in the cylinder 2 match the filling state of the $^{18}$O water which was previously set. To avoid the need for a reaction volume corresponding in amount to the target water volume for the subsequent nucleophilic ($^{18}$F) fluoridation, a displacement effect of the piston 4 is used. The piston 4 is shifted upwardly by a movement of the yoke 6 in this direction. Simultaneously the cannula 3 is shifted in the cylinder 2 corresponding to the height of the piston 4 out of the cylinder 2. The volume that thus must be introduced into the cylinder 2 must correspond to the volume of the gap 14 that is formed when the piston 4 projects into the cell 1 (see FIG. 2, Position II) such that the upper end of the piston 4 coincides with the fill level which has been determined by the ($^{18}$F) fluoride fixed on the surface of the cylinder 2. In an advantageous configuration of the device, the ratio of the volume ($V_1$) of the cylinder 2 to the volume ($V_3$) of the gap amounts to 4:1 to 10:1. In an especially preferred configuration of the device, it amounts to 4:1. With an $^{18}$O water volume of, for example 1.3 ml, the volume of the gap 14 at a fill level can amount to about 0.29 ml. When the piston is shifted upwardly sufficiently that the upper end of the piston 4 coincides with the fill level determined by the ($^{18}$F) fluoride fixed on the surface of the cylinder (see FIG. 2, piston B), the ($^{18}$F) fluoride can be transferred to the reaction solution by applying an electric belt (with the (Sigradur® as the cathode). In this position, only the gap volume 14 is filled. The solution is sealed at the lower end by two annular cylinders 15 and 16 (for example O-rings) with respect to the piston 4 so that a lateral outflow of liquid from the lower end of the cylinder is prevented.

For emptying the reaction vessel, the vessel 4 is again lowered and the liquid transported outwardly through the cannula 3 or the bore 5 of the piston 4.

In an advantageous configuration of the device and the method, the feed or the evacuation of the ($^{18}$F) fluoride-containing target water and the organic solvent are effected through different conduits. When, for example, the supply of the ($^{18}$F) fluoride-containing target water is effected through the conduit 3, the transport of the organic solvent which is used for desorption of the product is effected through the bore 5 to avoid a contamination of the conduit 3. Thus a high effort cleaning of the conduit for the target water can be avoided. The transport of the target water will be self-understood to be possible also through the bore 5 and the transport of the organic solvent correspondingly through the conduit 3. It is important for a device which can be easily manipulated and the method that a separate conduit is provided for each of the different liquids.

Through the method of the invention and the device it is possible to reduce the edict quantity. This reduction in the mass of the educt is especially advantageous for the subsequent chromatographic separation of the carrier-poor $^{18}$F-labeled product from the educt. In previously known methods and with previously known devices for the separation of the carrier-free radionuclide and its radiochemical reaction, the educt quantity is significantly greater. Through the method and device according to the invention, the volume of the educt solution and thus the quantity of the educt is reduced by a multiple (at least 3 to 4 times) so that the chromatographic separation of educt and the $^{18}$F-labeled product is significantly improved.

The reduction of the absolute educt quantity thus gives rise to a cost saving and therewith an improvement in the economy of the method.

EXAMPLE $^{18}$F-Leveling of N-Methylbenperidol

The ($^{18}$F) fluoride-containing $^{18}$O water (1.3 ml) coming from the target of the cyclotron is transported into the flow cell 1 through the bore 5 of the piston 4. Upon application of an electrical voltage of 20 volts from a direct current source 13 (anode=cylinder (2) of carbon glass), the carrier-poor radio isotope is identically adsorbed within about 8 minutes on the surface of the cylinder 2. The $^{18}$O water is driven out through the bore 5 by means of helium. To dry the cylinder wall, the flow cell is filled once or twice each with 1.6 ml of water-free dimethylsul-oxide (DMSO) and emptied through the cannula 3 serving as the counterelectrode. Through the cannula 3, a solution of 5 mg Kryptat ([$K \subset 2.2.2$]$_2$CO$_3$ in 300 µl DMSO) is introduced into the flow cell 1 and piston 4 shifted by a motor so that the liquid surface reaches the upper boundary of the anodically deposited $^{18}$F fluoride. The potential is reversed (−2V) and the cylinder is heated for 5 minutes to 100° C. After depolarization of the flow cell, the piston is brought into its lower position and through the cannula 3 of a solution of 2 mg of N-methyl-desfluor-nitro-benperidol in 150 µl of DMSO is supplied. The piston 4 is shifted again into the upper position and the flow cell is heated for 10 minutes to 150° C. Then the flow cell is cooled with compressed air to ambient temperature. The flow cell is emptied through the cannula 3, is washed with about 0.8 ml acetonitrile at 50° C. and this solution is mixed with the DMSO product solution by a subsequent HPL-chromatography, the radiotracer ($^{18}$F) N-methylbenperidol is purified and isolated.

The invention claimed is:

1. A flow cell for separating carrier-free radionuclides from liquid or liquefiable target material and its radiochemical reaction, the flow cell comprising
 a cylinder extending along and centered on an axis and having upper and lower ends;
 a cannula extending axially in the cylinder from one of the cylinder ends and having a cannula end in the cylinder;
 a piston extending axially in the cylinder from the other of the cylinder ends and having a piston end spacedly juxtaposed with the cannula end, the piston having an outer surface separated from an inner surface of the cylinder by a gap between cylinder and the piston, a volume ratio between the cylinder and the gap being equal to between 4.1 and 10.1; and
 supply means for applying a voltage differential between the inner surface of the cylinder and the cannula.

2. The flow cell according to claim 1 wherein a diameter of the piston is smaller than an inside diameter of the cylinder.

3. The flow cell according to claim 1 wherein the piston is comprised of chemically inert material.

4. The flow cell according to claim 1 wherein the piston is composed of PEEK, implement glass or quartz glass.

5. The flow cell according to claim 1 wherein the piston has a bore, the cell further comprising means for feeding a fluid through the bore.

6. The flow cell according to claim 1 wherein the piston has a central bore, the cell further comprising means for feeding a fluid through the bore.

7. The flow cell according to claim 1 wherein the cylinder has a pore-free inert surface.

8. The flow cell according to claim 1 wherein the cylinder is composed of chemically inert material.

9. The flow cell according to claim 1 wherein the cylinder is composed of carbon glass, a noble metal or platinum.

10. The flow cell according to claim 1 wherein the inner surface of the cylinder is electrically charged by the supply means.

11. The flow cell according to claim 1 wherein the cannula is electrically charged by the supply means.

12. The flow cell according to claim 1 wherein the cannula is the counter electrode to the electrically charged cylinder.

* * * * *